US00PP37283P2

(12) United States Plant Patent
Gray-Jones

(10) Patent No.: US PP37,283 P2
(45) Date of Patent: Feb. 24, 2026

(54) STRAWBERRY PLANT NAMED 'SB_17_122-093'

(50) Latin Name: *Fragaria ananassa*
Varietal Denomination: SB_17_122-093

(71) Applicant: PLANT SCIENCES GENETICS, INC., Watsonville, CA (US)

(72) Inventor: Kendra M. Gray-Jones, Archer, FL (US)

(73) Assignee: Plant Sciences Genetics, Inc., Watsonville, CA (US)

( * ) Notice: Subject to any disclaimer, the term of this patent is extended or adjusted under 35 U.S.C. 154(b) by 0 days.

(21) Appl. No.: 19/271,469

(22) Filed: Jul. 16, 2025

(51) Int. Cl.
*A01H 5/08* (2018.01)

(52) U.S. Cl.
USPC ..... Plt./208

(58) Field of Classification Search
USPC ..... Plt./208
CPC ..... A01H 6/7409; A01H 5/08
See application file for complete search history.

(56) References Cited

U.S. PATENT DOCUMENTS

| | | | |
|---|---|---|---|
| PP30,564 | P3 | 6/2019 | Whitaker |
| PP33,359 | P2 | 8/2021 | Blaker et al. |
| PP35,234 | P2 | 6/2023 | Blaker |

*Primary Examiner* — Keith O. Robinson
(74) *Attorney, Agent, or Firm* — Foley & Lardner LLP

(57) ABSTRACT

This invention relates to a new and distinct variety of strawberry plant named 'SB_17_122-093'. This new strawberry plant named 'SB_17_122-093' is primarily adapted to the growing conditions of West Central Florida, and is primarily characterized by achenes set even with the surface of the fruit; vigorous plant habit; high marketable yield; early time of first flower and fruit; and very large berry size.

4 Drawing Sheets

Latin name of the genus and species of the plant claimed: *Fragaria ananassa.*

Variety denomination: 'SB_17_122-093'.

BACKGROUND OF THE INVENTION

The present invention relates to a new and distinct strawberry variety named 'SB_17_122-093'. This new variety is a result of a controlled cross made in 2017 in an ongoing breeding program between the patented strawberry breeding selection designated 'SB_14_223-007' (U.S. Plant Pat. No. 35,234 P2) as the seed (female) parent, and the patented strawberry breeding selection designated 'SB_12_53-118' (U.S. Plant Pat. No. 33,359 P2), as the pollen (male) parent. The variety is botanically known as *Fragaria ananassa.*

The seedling resulting from the aforementioned cross was selected from a controlled breeding plot in Hillsborough County, Florida in the fall/winter of 2018-2019. After its selection, the new variety was asexually propagated by stolons in both Siskiyou County, California and San Joaquin County, California. The new variety was extensively tested over the next several years in fruiting fields in Hillsborough County, Florida. This propagation has demonstrated that the combination of traits disclosed herein as characterizing the new variety are fixed and remain true-to-type through successive generations of asexual reproduction.

BRIEF SUMMARY OF THE INVENTION

'SB_17_122-093' is primarily adapted to the climate and growing conditions of West Central Florida. The subtropical climate of West Central Florida provides the day length and moderate temperatures needed to produce an early yielding, vigorous plant and maintain fruit quality during the fall and winter production months.

The following traits have been repeatedly observed and are determined to be unique characteristics of 'SB_17_122-093', which in combination distinguish this strawberry plant as a new and distinct variety:

1. Achenes typically set even with the surface of the fruit;
2. Vigorous plant habit;
3. High marketable yield;
4. Early time of first flower and fruit; and
5. Very large berry size.

'Florida Brilliance' (U.S. Plant Pat. No. 30,564) is currently the dominant strawberry variety in Hillsborough County, Florida. The fruits of 'SB_17_122-093' are similar in skin integrity, the level of sunken seeds, and berry shape to 'Florida Brilliance', but the fruit color of 'Florida Brilliance' is slightly lighter than the fruits of 'SB_17_122-093'. The plants of 'SB_17_122-093' are similar in vigor, openness of architecture, and uniformity to 'Florida Brilliance', but have more runners per plant than 'Florida Brilliance'. In side-by-side comparisons from the 2024-2025 season (Dec. 5, 2024 to Mar. 15, 2025), 'SB_17_122-093' compares with 'Florida Brilliance' (U.S. Plant Pat. No. 30,564) in the following combination of characteristics as described in Table 1.

TABLE 1

| Characteristic | 'SB_17_122-093' | 'Florida Brilliance' (U.S. Plant Pat. No. 30,564) |
|---|---|---|
| Dec. marketable yield (gm/plt) | 62 | 47 |

TABLE 1-continued

| Characteristic | 'SB_17_122-093' | 'Florida Brilliance' (U.S. Plant Pat. No. 30,564) |
|---|---|---|
| Season marketable yield (gm/plt) | 315 | 323 |
| Dec. average berry size (gm) | 20.5 | 17.8 |
| Plant: density (1-5:dense-open) | 3.0 | 4.0 |

For identification, a series of molecular markers have been determined for this new variety.

In side-by-side comparisons from the 2024-2025 season (Dec. 5, 2024 to Mar. 15, 2025), 'SB_17_122-093' compares with its parents, 'SB_14_223-007' (U.S. Plant Pat. No. 35,234 P2) and 'SB_12_53-118' (U.S. Plant Pat. No. 33,359 P2), by the following combination of characteristics as described in Tables 2 and 3.

TABLE 2

| Characteristic | 'SB_17_122-093' | 'SB_14_223-007' (U.S. Plant Pat. No. 35,234 P2) |
|---|---|---|
| Dec. marketable yield (gm/plt) | 62 | 100 |
| Season marketable yield (gm/plt) | 315 | 293 |
| Dec. average berry size (gm) | 20.5 | 27.7 |
| Plant: seed position | Even | Slightly above |

TABLE 3

| Characteristic | 'SB_17_122-093' | 'SB_12_53-118' (U.S. Plant Pat. No. 33,359 P2) |
|---|---|---|
| Dec. marketable yield (gm/plt) | 62 | 128 |
| Season marketable yield (gm/plt) | 315 | 453 |
| Dec. average berry size (gm) | 20.5 | 24.5 |
| Season average berry size (gm) | 23.0 | 26.0 |

BRIEF DESCRIPTIONS OF THE PHOTOGRAPHS

The accompanying color photographs illustrate the overall appearance of typical specimens of the new strawberry variety 'SB_17_122-093' at various stages of development, as true as it is reasonably possible with color reproductions of this type. Color in the photographs may differ slightly from the color value cited in the botanical descriptions which accurately describe the color of 'SB_17_122-093'. The depicted plant and plant parts of the new strawberry variety 'SB_17_122-093' are approximately four months old. The photographs were taken in Hillsborough County, Florida.

DETAILED BOTANICAL DESCRIPTION

Figure 1:
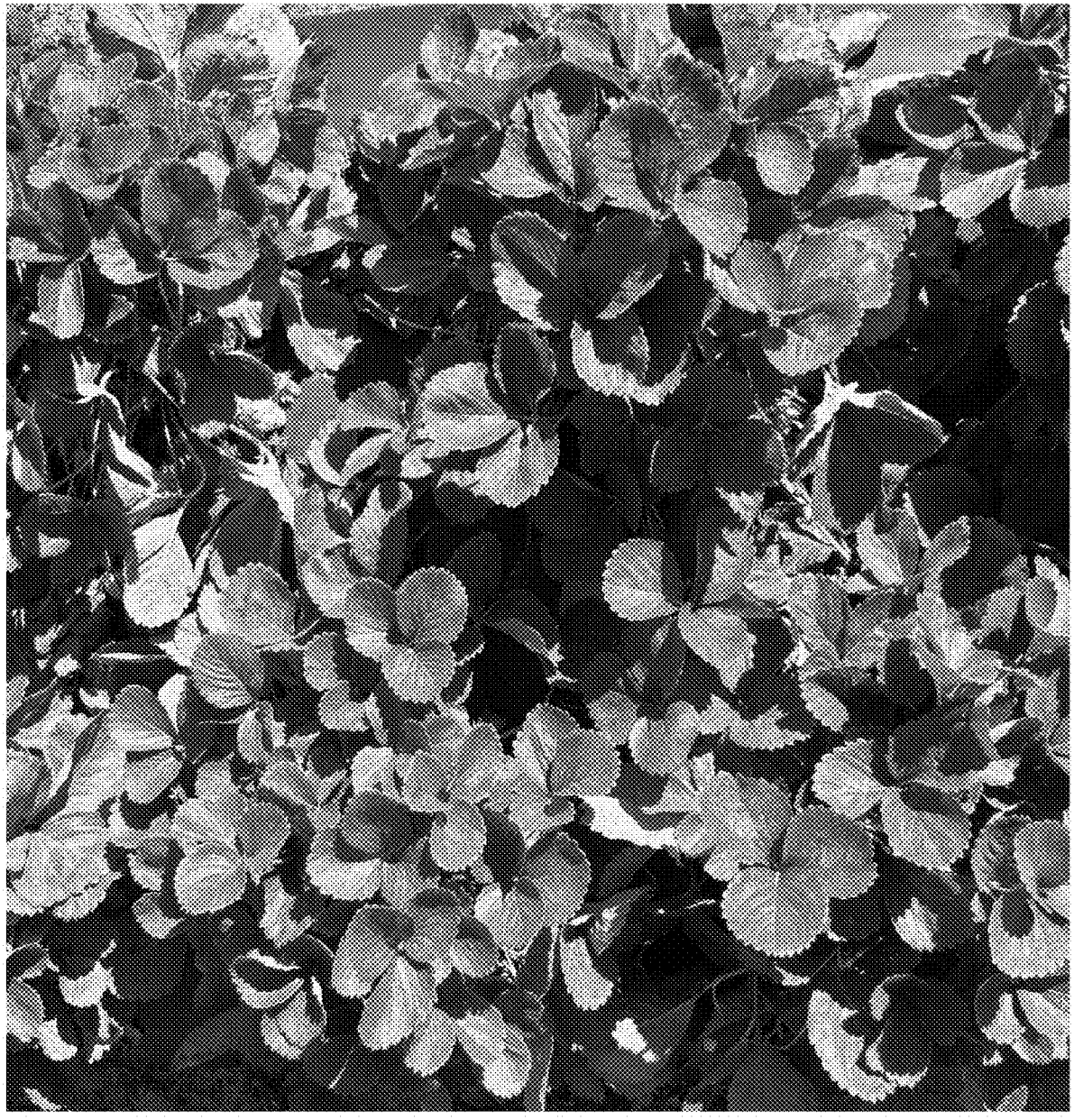
FIG. 1 shows typical fruiting field characteristics of 'SB_17_122-093', taken in the month of March 2025.
Figure 2:
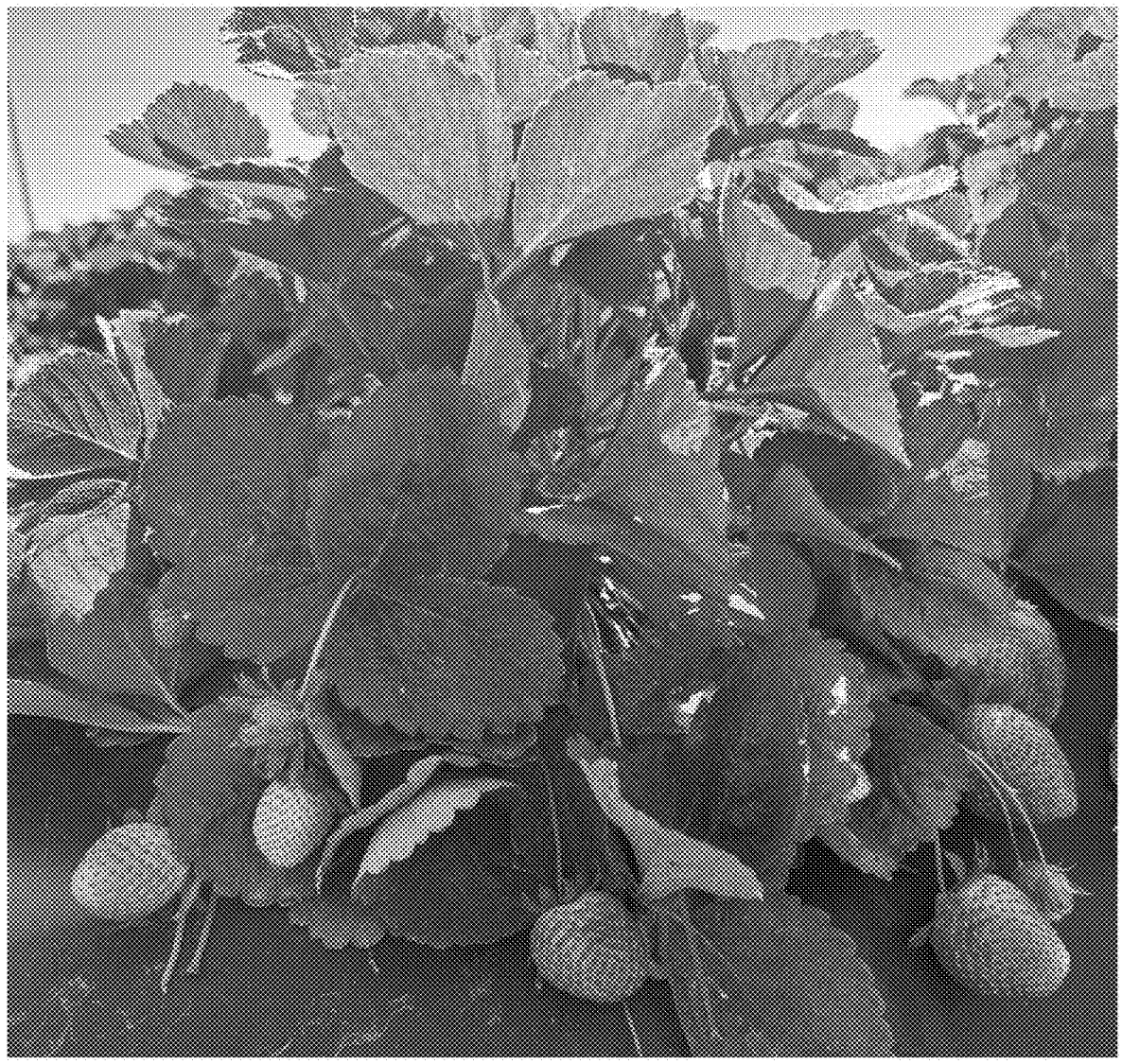
FIG. 2 shows a close-up view of a typical plant of 'SB_17_122-093', taken in the month of March 2025.
Figure 3:
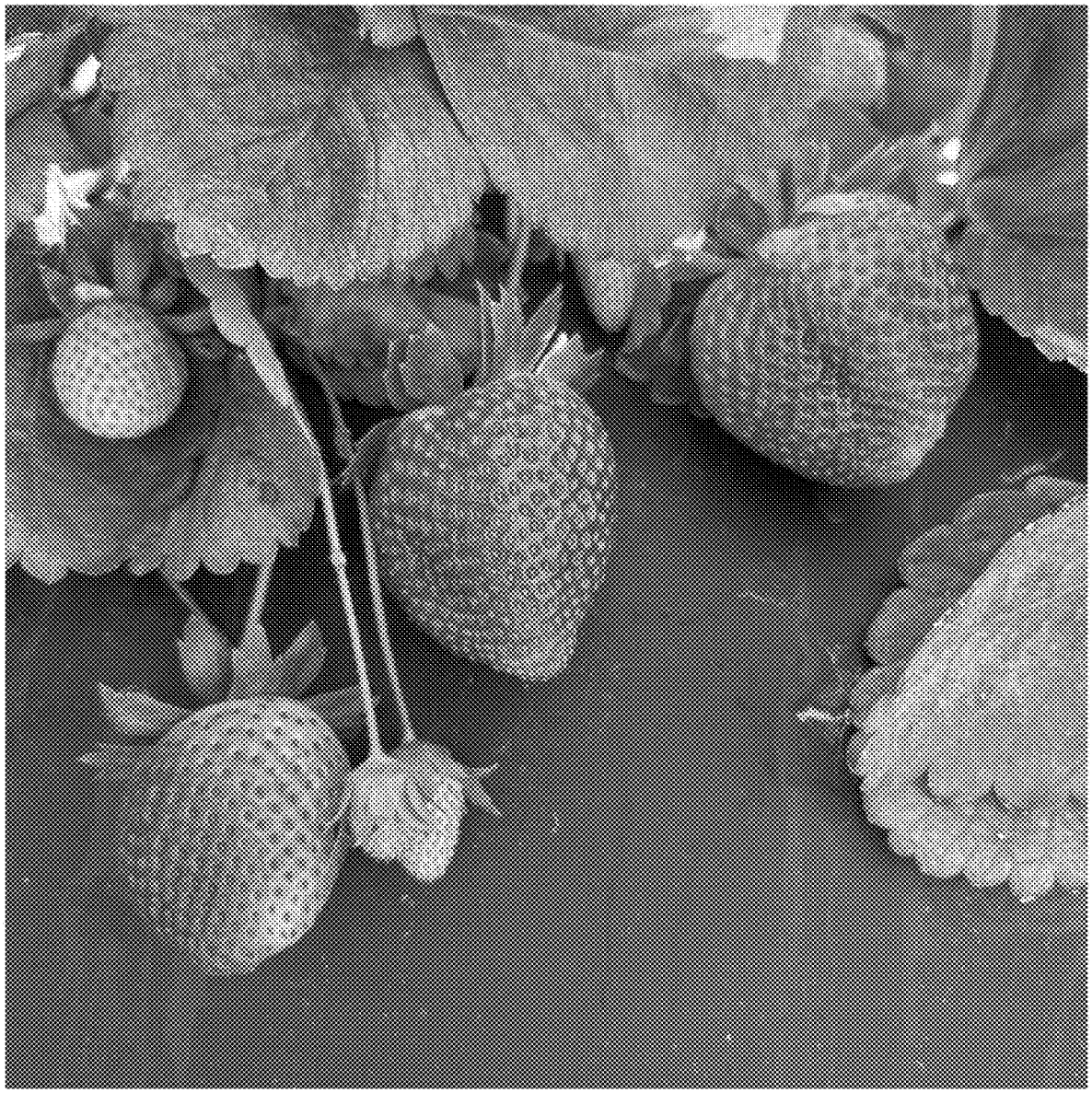
FIG. 3 shows typical mature and immature field fruit of 'SB_17_122-093', taken in the month of March 2025.
Figure 4:
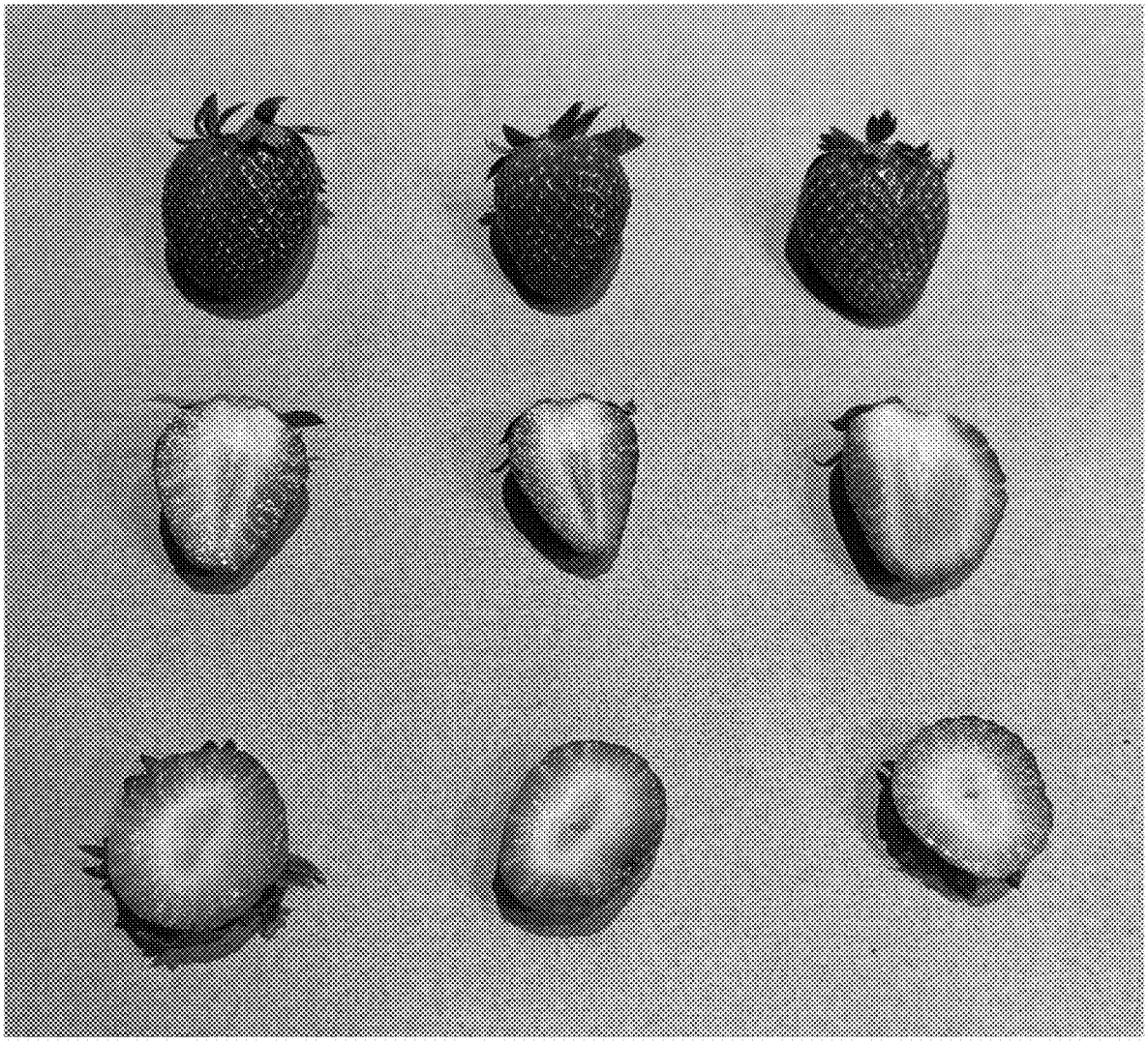
FIG. 4 shows typical internal and external mature fruit characteristics of 'SB_17_122-093', taken in the month of March 2025.

The new variety 'SB_17_122-093' has not been observed under all possible environmental conditions. The characteristics of the new variety 'SB_17_122-093' may vary in detail, depending upon variations in environmental factors, including weather (temperature, humidity and light intensity), day length, soil type and location. In addition, the characteristics of any parental variety or comparison variety included in Table 1 of the present invention may vary in detail, depending upon variations in environmental factors, including weather (temperature, humidity and light intensity), day length, soil type and location.

The aforementioned photographs, together with the following description of the new varieties 'SB_17_122-093', unless otherwise noted, are based on observations taken during the 2022-2023 growing season in Hillsborough County, Florida. These measurements and ratings were taken from plants of 'SB_17_122-093' dug from a high-elevation nursery located in Siskiyou County, California during mid-September 2024 and planted approximately one month later in Hillsborough County, Florida. The planting date was significantly delayed due to a series of hurricanes across Florida during the month of October 2024. The approximate age of the observed plants is four to five months. Yield observations including average weight and marketable yield, along with fruit quality characteristic, were measured during the 2024-2025 growing season. Flower measurements and characteristics are from secondary flowers unless otherwise noted. Fruit characteristics and measurements are from secondary fruit, unless otherwise noted.

Where noted, color terminology follows the Royal Horticultural Society Colour Chart, London, Sixth Edition (2019 Reprint).

The following characteristics describe fruit, plant, stolon, foliage, fruiting truss, flower, reproductive organs and pest and disease characteristics of the new strawberry 'SB_17_122-093'.

Fruit characteristics:

*Color of mature fruit*—RHS N45A (red group).
*Color of internal flesh (excluding core)*—RHS 44A (red group).
*Color of core*—RHS 44C (red group).
*Average length (cm)*—4.0.
*Average width (cm)*—3.4.
*Size*—Very Large.
*Average length/width ratio*—1.19 (slightly longer than broad).
*Average calyx diameter (cm)*—4.14.
*Season average weight (gm)*—23.6.
*Average achenes per berry*—295.2.
*Average achene length (mm)*—1.9.
*Average achene width (mm)*—0.9.
*Season marketable yield (gm/plant)*—354.
*Predominant shape*—Conical.
*Difference in shape between primary and secondary fruit*—Moderate.
*Band without achenes*—Narrow.

*Evenness of surface*—Even.
*Evenness of color*—Even.
*Glossiness*—Medium.
*Insertion of achenes*—Level with surface.
*Position of calyx attachment*—Inserted.
*Attitude of sepals*—Downward and Outward.
*Size of calyx in relation to fruit diameter*—Smaller.
*Adherence of calyx* (*when fully ripe*)—Medium.
*Firmness of flesh* (*gf*)—366.
*Distribution of red color of the flesh*—Marginal and moderately central.
*Hollow center expression*—Weak.
*Time of first flowering*—Early (mid to late-October in Hillsborough County, Florida).
*Flowering season*—October-February.
*Time of first fruit*—Early (late-November in Hillsborough County, Florida).
*Fruiting season*—November-March.
*Post-harvest fruit longevity*—9-11 days, if stored according to industry standards.
*Type of bearing*—Not remontant.

Plant characteristics:
*Average height* (*cm*)—24.9.
*Average spread* (*cm*)—45.6.
*Size*—Large.
*Habit*—Upright.
*Density*—Medium.
*Vigor*—Strong.

Stolon characteristics:
*Color*—RHS N144A (yellow-green group).
*Anthocyanin coloration*—RHS 180C (greyed-red group).
*Anthocyanin intensity*—Ranges from medium to weak.
*Pubescence*—Ranges from medium to sparse.
*Attitude of hairs*—Upward.

Terminal leaflet characteristics:
*Color of upper surface*—N137A (green group).
*Color of underside*—RHS 136B (green group).
*Average length* (*cm*)—8.8.
*Average width* (*cm*)—8.1.
*Average area terminal* ($cm^2$)—71.5.
*Average length/width ratio*—1.09 (longer than broad).
*Shape of base*—Obtuse.
*Margins* (*shape of teeth*)—Serrate to crenate.
*Average serrations per leaf*—17.4.

Foliage characteristics:
*Color of upper surface*—RHS N147A (green group).
*Color of underside*—RHS 147B (green group).
*Number of leaflets*—3.
*Leaf size*—Medium.
Average *length* (*cm*)—13.4.
*Average width* (*cm*)—15.9.
*Average area foliage* ($cm^2$)—213.12.
*Shape in cross section*—Moderately Concave.
*Texture/interveinal blistering*—Medium.
*Leaf glossiness*—Medium.
*Leaf variegation*—Absent.
*Venation pattern*—Pinnate.
*Apex descriptor*—Obtuse.

Petiole characteristics:
*Petiole color*—RHS N144C (yellow-green group).
*Average length* (*cm*)—15.13.
*Average diameter* (*mm*)—2.65.
*Petiolule color*—RHS 144D (yellow-green group).
*Petiolule average length* (*mm*)—8.38.
*Average petiolule diameter* (*mm*)—1.82.
*Attitude of hairs*—Strongly outward.
*Texture*—Slightly Moderate.
*Frequency of bract leaflets*—20%.
*Size of bract leaflets*—Small.
*Pubescence*—Slightly Moderate.

Stipule characteristics:
Color—RHS 145A (yellow-green group).
Anthocyanin coloration—RHS 182D (greyed-red group).
Anthocyanin intensity—None.
Average length (mm)—38.4.
Average width (mm)—10.5.
Base descriptor—Truncate.
Apex descriptor—Obtuse.
Shape—Triangular.
Margin—Smooth.
Texture—Moderate.

Fruiting truss characteristics:
*Anthocyanin coloration*—N/A.
*Anthocyanin intensity*—Absent.
*Pubescence*—Medium.
*Attitude at first pick*—Prostrate.
*Position relative to foliage*—Ranges from level with to below.
*Flower quantity* (*average per plant season long*)—42.
*Average fruits per truss*—5.5.
*Pedicel attitude of hairs*—Slightly outward.
*Average pedicel length* (*cm*)—10.13.
*Average pedicel diameter* (*mm*)—1.62.
*Pedicel texture*—Moderate to Smooth.
*Pedicel color*—RHS 144C (yellow-green group).
*Average peduncle length* (*cm*)—6.8.
*Average peduncle diameter* (*mm*)—3.1.
*Peduncle texture*—Moderate to Smooth.
*Peduncle color*—144D (yellow-green group).

Flower characteristics:
*Flower bud shape*—Pyriform.
*Average flower bud length* (*mm*)—21.0.
*Average flower bud diameter* (*mm*)—9.0.
*Flower bud color*—RHS 146C (yellow-green group).
*Flower depth* (*mm*)—11.2.
*Corolla* (*flower*) *average diameter* (*mm*)—38.8 (ranges from medium to large).
*Upper petal color*—RHS NN155C (white group).
*Lower petal color*—RHS NN155C (white group).
*Petal shape*—Orbicular.
*Petal apex descriptor*—Obtuse.
*Petal margin*—Smooth.
*Petal base*—Decurrent.
*Petal texture*—Smooth.
*Petal average length* (*mm*)—14.5.
*Petal average width* (*mm*)—12.2.
*Petal average length/width ratio*—1.2 (slightly longer than broad).
*Average petals per flower*—7.4.
*Relative position of petals* (*flowers with 5 or 6 petals*)—Overlapping.
*Upper sepal color*—RHS 143A (green group).
*Lower sepal color*—RHS 143C (green group).
*Sepal shape*—Cuneate.
*Sepal apex descriptor*—Obtuse.
*Sepal margin*—Serrate.
*Sepal texture*—Smooth.
*Sepal average length* (*mm*)—22.7.

*Sepal average width* (*mm*)—11.8.
*Sepal average length/width ratio*—1.9.
*Average sepals per flower*—13.8.
*Calyx average diameter* (*mm*)—56.7.
*Size of calyx relative to corolla*—Larger.
*Size of inner calyx relative to outer calyx*—Same.

Reproductive organs:

*Receptacle color*—RHS 144A (yellow-green group).
*Pollen color*—RHS 13A (yellow group).
*Stamen*—Present.
*Average filament length* (*mm*)—3.05.
*Filament color*—RHS 157A (green-white group).
*Average anther length* (*mm*)—1.76.
*Anther shape*—Ovoid.
*Anther color*—RHS 13A (yellow-orange color).
*Average pistils per flower*—295.2.
*Pistil length* (*mm*)—0.5-1.5.
*Style length* (*mm*)—0.5 to 1.
*Style color*—RHS 1D (green-yellow group).
*Stigma diameter* (*mm*)—<0.1.
*Stigma shape*—Simple.
*Ovary color*—RHS 1A (green-yellow group).
Pollen amount—Abundant.

Disease and Pest Reactions:

*Fusarium wilt* (*Fusarium oxysporum*)—Susceptible.
*Phytophthora crown rot* (*Phytophthora cactorum*)—Susceptible.

I claim:

1. A new and distinct strawberry plant named 'SB_17_122-093', as herein described and illustrated in the specification.

* * * * *